United States Patent [19]

Schally et al.

[11] Patent Number: 4,914,189

[45] Date of Patent: Apr. 3, 1990

[54] SYNTHETIC GHRH ANALOGS

[75] Inventors: Andrew V. Schally, Metairie, La.; Jozsef Gulyas, Budapest, Hungary; Sandor Bajusz, New Orleans, La.

[73] Assignee: The Adminstrators of the Tulane Educational Fund, New Orleans, La.

[21] Appl. No.: 11,152

[22] Filed: Feb. 5, 1987

[51] Int. Cl.$^4$ .............................................. C07K 7/10
[52] U.S. Cl. ..................................................... 530/324
[58] Field of Search .................. 530/324, 313; 514/20, 514/806, 12

[56] References Cited

U.S. PATENT DOCUMENTS

| | | | |
|---|---|---|---|
| 4,528,190 | 7/1985 | Vale, Jr. et al. | 530/324 |
| 4,622,312 | 11/1986 | Felix et al. | 530/324 |
| 4,659,693 | 4/1987 | Nestor . | |

FOREIGN PATENT DOCUMENTS

| | | | |
|---|---|---|---|
| 0192492 | 8/1986 | European Pat. Off. | 530/329 |
| 62-190198 | 8/1987 | Japan . | |

OTHER PUBLICATIONS

Chem. Abs., vol. 97, 1982, 195098W.
Chem. Abs., vol. 107, 1987, 131274t.
Coy et al., Peptides 7, 49–52, (1986).
Kovacs, et al., Life Science, 42, 27–35, (1988).
Sato et al., Biochem. Biophys. Research Communication, 149, 531–537, (1987).
Chemical Abstracts, vol. 102, 1985, 149761f.

*Primary Examiner*—Delbert R. Phillips
*Attorney, Agent, or Firm*—Omri M. Behr

[57] ABSTRACT

Human pancreatic GRF (hpGRF), rat hypothalamic GRF (rGRF) and porcine hypothalamic GRF (pGRF) have been earlier characterized and synthesized. The invention provides synthetic peptides which are extremely potent in stimulating the release of pituitary GH in animals, including humans, which have resistance to enzymatic degradation in the body, and which have the sequence:

$$Q^1-CO-R_2-R_3-Ala_4-Ile_5-Phe_6-Thr_7-R_8-Ser_9-R_{10}-Arg_{11}-R_{12}-R_{13}-R_{14}-R_{15}-Gln_{16}-R_{17}-R_{18}-Ala_{19}-Arg_{20}-Lys_{21}-Leu_{22}-R_{23}-R_{24}-R_{25}-Ile_{26}-R_{27}-R_{28}-NH-Q^2$$

wherein
$Q^1$ is an omega or alpha-omega substituted alkyl,
$Q^2$ is a lower omega-quanidino-alkyl group.
$R_2$ is Ala, D-Ala, or D-N-Methyl-Ala
$R_3$ is Asp, D-Asp, Glu, or D-Glu
$R_8$ is Asn, D-Asn, Ser, or D-Ser
$R_{10}$ is Tyr or D-Tyr
$R_{12}$ is Lys, D-Lys Arg or Orn
$R_{13}$ is Val or Ile
$R_{14}$ is Leu or D-Leu
$R_{15}$ is Gly, N-Methyl-Gly, or D-Ala
$R_{17}$ is Leu or D-Leu
$R_{18}$ is Tyr or Ser
$R_{23}$ is Leu or D-Leu
$R_{24}$ is Gln or His
$R_{25}$ is Asp, D-Asp, Glu, or D-Glu
$R_{27}$ is Met, D-Met, Ala, Nle, Ile, Val, Nva, Leu
$R_{28}$ is Asn or Ser The peptides as well as nontoxic salts thereof may be administered to animals, including humans and cold-blooded animals, to stimulate the release of GH and may be used diagnostically.

8 Claims, 1 Drawing Sheet

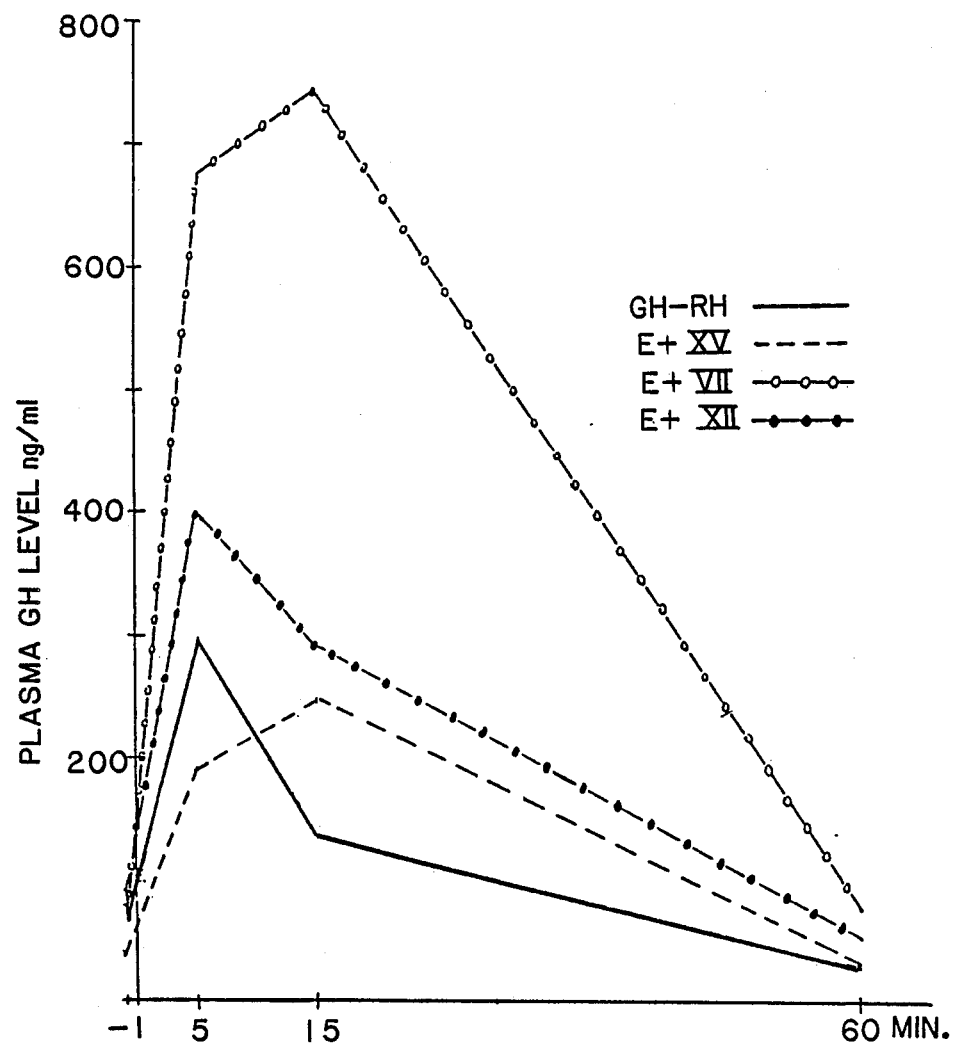

SYNTHETIC GHRH ANALOGS

This invention was made in part, with Government support under Grant No. AM 074.67, awarded by the NIH-NIADDKD. The Government has certain rights in this application.

The present invention relates to peptides having influence on the function of the pituitary gland in humans and other animals. In particular, the present invention is directed to a peptide which promotes the release of growth hormone by the pituitary gland.

BACKGROUND OF THE INVENTION

Physiologists have long recognized that the hypothalamus controls the secretory functions of the adenohypophysis with the hypothalamus producing special substances which stimulate or inhibit the secretion of each pituitary hormone. Hypothalamic releasing factors have been characterized for the pituitary hormone thyrotropin (the tripeptide TRF), for the pituitary gonadotropins luteinising hormone and follicle stimulating hormone (the decapeptide LRF, LH-RH or GnRH) and for the pituitary hormone and adreno-corticotropin (the 41-amino acid polypeptide CRF). An inhibitory factor, called somatostatin, has also been characterized in the form of a tetradecapeptide which inhibits the secretion of growth hormone (GH). GH releasing factors (GRFs) have been isolated from human pancreatic tumor as well as rat, porcine, borine, ovine, caprine and human hypothalami. With the exception of the rat, all characterized GRFs containing 44 amino acids with an amidated carboxy-terminus. Each of these hypophysiotropic factors has been reproduced by total synthesis. Analogs of the native structures have also been synthesized in order to elucidate structure-activity relationships and, eventually, to provide synthetic congeners with improved properties, such as increased hormonal activity and/or 10 metabolic stability Studies with the synthetic human growth hormone releasing factor (hGRF and its analogs (N. Ling., et al, Biochem. Biophys. Res. Commun., (1984), vol. 122, pp. 304–310; vol. 123, pp. 854–861; V. A. Lance, et al., Biochem. Biophys. Res. Commun., 1984, vol. 119, pp. 165–272)) have revealed that (a) deletion of the $NH_2$-terminal tyrosine residue of hGRF causes its activity to drop to 0.1%; N-acetylation of this residue or change of replacement of L by D isomers lowers the in vitro bioactivity of hGRF (1–40-)—OH to 2–3%, and causes a 10–12 fold increase in the in vivo potency of hGRF(1-29)—$NH_2$; these findings indicate that the presence of said residue is essential for imparting the hGRF molecule with high bioactivity;

(b) fragments containing the first 29 residues at least, e.g., hGRF(1-29)—$NH_2$ and hGRF(1-37)—$NH_2$, have at least 50% of the potency of hGRF; further deletion of amino acids results in a marked decrease in bioactivity, 30 e.g., hGRF(1-27)—$NH_2$ and hGRF(1-23)—$NH_2$ exhibit 12% and 0.24% of the potency of hGRF, respectively; these findings indicate the significance of the arginine residue at position 29 of hGRF. It is also known that the 4-guanidino-butylamino group, the so-called agmatine (Agm) residue, can play the role of the arginine residue in certain peptides and has some influence in providing resistance to enzymatic degradation (S. Bajusz, et al., in: PEPTIDES, 1982, (K. Blaha and P. Melon, eds.), Walter Gruyter, Berlin-New York, 1983, pp. 643–647). Classical (solution) methods have only been employed for the preparation of agmatine peptides to date; it is desired to provide methodology for the solid-phase synthesis of these peptides using techniques of peptide synthesis which have proven to be suitable for preparing GRFs and their analogs.

SUMMARY OF THE INVENTION

There is provided a novel series of synthetic peptides which are extremely potent in stimulating the release of pituitary GH in animals, including humans, which are resistant to enzymatic degradation in the body in view of the provision of an omega-guanidino lower alkyl group at the terminal 28-position of the peptide. There are also provided several methods of attaching said omega-guanidino alkyl group to a support phase procedures for building up the aforesaid peptide by means of a Merrifield solid phase synthesizer and procedures for cleaving said peptide from said support phase The ultimate products of the present invention are peptides (abbreviated [PeP]) having the sequence:

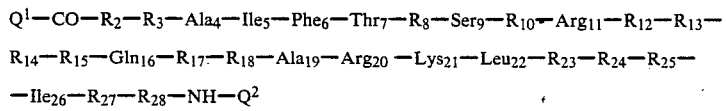

wherein $Q^1$ is an omega or alpha-omega substituted alkyl of the structure:

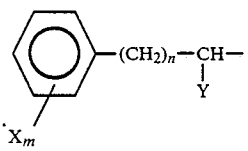

or

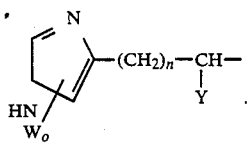

where:
X=H,OH
Y=H,OH,$NH_2$, $CH_3CONH$
W=lower alkyl, or haloalkyl wherein halo is chloro or fluoro and alkyl is 1–5 carbon atoms
m=1,2
n=0,1,2
o=0,1
$R_2$ is Ala,D-Ala, or D-N-Methyl-Ala
$R_3$ is Asp,D-Asp,Glu,or D-Glu
$R_8$ is Asn,D-Asn,Ser, or D-Ser
$R_{10}$ is Tyr or D-Tyr
$R_{12}$ is Lys, D-Lys Arg or Orn
$R_{13}$ is Val or Ile
$R_{14}$ is Leu or D-Leu
$R_{15}$ is Gly,N-Methyl-Gly, or D-Ala $R_{17}$ is Leu or D-Leu
$R_{18}$ is Tyr or Ser
$R_{23}$ is Leu or D-Leu
$R_{24}$ is Gln or His
$R_{25}$ is Asp,D-Asp,Glu, or D-Glu
$R_{27}$ is Met,D-Met,Ala,Nle,Ile,Val,Nva,Leu
$R_{28}$ is Asn or Ser
$Q^2$ is a lower omega-guanidino-alkyl group having a formula:

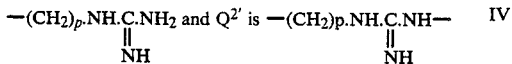
(IV)

wherein p=2-6 and the pharmaceutically acceptable salts addition thereof with the pharmaceutically acceptable organic or inorganic bases and organic or inorganic acids The peptides of the present invention [PeP] are synthesized in accordance with the following procedures.

In the first method, the $Q^2$ segment of $NH_2$—$Q^2$ moiety to a support phase [SP] selected from the group consisting of amino resins and hydroxyl type resins which comprises the sequential steps of reacting a t-butoxycarbonylating agent with $NH_2.Q^2$ in the presence of a base to form Boc-NH.$Q^2$, (V) reacting said Boc-NH.$Q^2$ with an arylsulphonyl halide suitably of the formula:

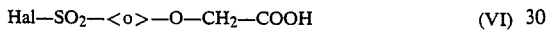
(VI)

wherein Hal is chloro or bromo, and <o> signifies (throughout the application) an unsubstituted benzene ring, at between −5° and 10° C. in a water soluble ether in the presence of aqueous alkali to form the corresponding

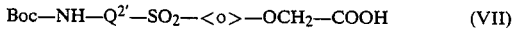
(VII)

which is coupled to the support phase [SP] by the action of a diloweralkyl carbodiimide to yield:

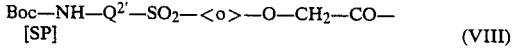
(VIII)

It is generally preferred that the support phase [SP] is an amino resin of the formula

(IX)

where [Pm] is a polymeric substrate.

This approach contemplates building the peptide sequence by the Boc protocol which is discussed in detail hereinbelow.

In an alternate embodiment which also contemplates the use of the Boc protocol, the Boc-NH-$Q^2$ is reacted with

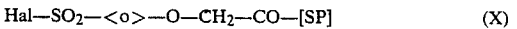
(X)

wherein Hal is bromo or chloro, to yield

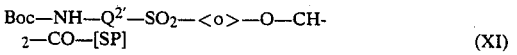
(XI)

Yet another embodiment is available for attaching the guanidino alkyl group to the support phase This method comprises the sequential steps of reacting N-benzyloxy carbonyl chloride with $NH_2.Q^2$ in the presence of a base to form Cbz-NH.$Q^2$, reacting said Cbz-NH.$Q^2$ with a substituted arylsulphonyl chloride of the formula:

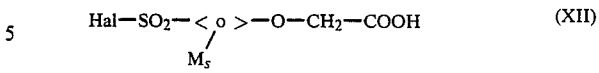
(XII)

wherein Hal is chloro or bromo , M is lower alkyl or lower alkoxy of 1 to 5 carbon atoms, and is 1-3, in the presence of a strong aqueous base and removing the Cbz group by catalytic hydrogenation to yield

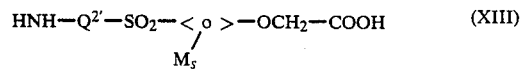
(XIII)

reacting this product with 9-fluorenylmethoxy carbonyl chloride in the presence of a base to yield

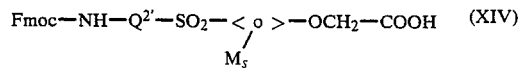
(XIV)

coupling this product to said support phase [SP] to yield

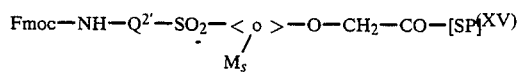
(XV)

As indicated, this procedure is preferred when it is intended to use the Fmoc protocol which is also set forth in detail hereinbelow.

Utilizing the aforementioned protected amino-alkyl-guanidino sulfophenoxy-acetyl-support phase as the terminal, the desired peptide itself is built up in the conventional manner for solid phase synthesis utilizing the protective groups and the specific procedures set forth in detail hereinbelow. When the synthesis is complete, the guanidino alkyl end of the peptide is cleaved from the sulfonyl group to which it is attached by one or two procedures. If the Boc protocol is utilized then the cleaving agent is anhydrous hydrofluoric acid, on the other hand, in the Fmoc protocol the cleaving agent is trifluoroacetic acid.

The pharmaceutical compositions in accordance with the invention include the peptides of Formula I, or a nontoxic salt of any of these, dispersed in a pharmaceutically or veterinarily acceptable liquid or solid carrier. Such pharmacetical compositions can be used in clinical medicine, both human and veterinary, for administration for therapeutic purposes, and also diagnostically. Moreover, they can be used to promote the growth of warm-blooded animals, including fowl, and in aquivulture for cold-blooded animals, e g., fish, eels, etc.

BRIEF DESCRIPTION OF THE DRAWINGS

FIG. 1 is a plot of Plasma GH levels against time in rats.

DESCRIPTION OF THE PREFERRED EMBODIMENTS

The nomenclature used to define the peptides is that specified by the IUPAC-IUB Commission on Biochemical Nomenclature (*European J. Biochem.*, 1984, 138, 9-37), wherein in accordance with conventional representation the amino groups at the N-terminus appears to the left and the carboxyl group at the C-terminus to the right By natural amino acid is meant one of common, naturally occurring amino acids found in proteins comprising Gly, Ala, Val, Leu, Ile, Ser, Thr, Lys, Arg, Asp, Asn, Glu, Gln, Cys, Met, Phe, Tyr, Pro, Trp and His By Nle is meant norleucine, by Nva is meant norvaline and by MeAla is meant N-methyl-alanine. When the amino acid residue has isomeric forms, it is the L-form of the amino acid that is represented unless otherwise expressly indicated.

Other abbreviations used are:

| | |
|---|---|
| AcOH | acetic acid |
| AcOEt | ethyl acetate |
| Ac$_2$O | acetic anhydride |
| Boc- | tert.butyloxycarbonyl- |
| DIC | diisopropylcarbodiimide |
| DIEA | diisopropylethylamine |
| DMF | dimethylformamide |
| HOBt | 1-hydroxybenzenetriazole hydrate |
| HPLC | high performance liquid chromatography |
| Fmoc- | fluorenylmethyoxycarbonyl- |
| MeOH | methyl alcohol |
| TEA | triethylamine |
| DCCI | dicyclohexylcabodiimide |
| 2-Cl-Z | 2-chloro-benzyloxycarbonyl |
| DCB | 2,6-dichlorobenzyl |
| Tos | p-toluenesulfonyl |
| TFA | trifluoroacetic acid |
| Cbz | benzyloxycarbonyl |

The procedures of the present invention may be carried out using a variety of support phases. These support phases may be amino or hydroxy resins such as amino methyl resins (suitably 1% cross linked), benzhydrylamine resins (suitably 2% cross linked), methylbenzhydrylamine resins (suitably 2% cross linked) and the like.

As starting material in the process, there may be utilized any amino lower alkyl guanidine having between 2 and 6, suitably 3 thru 5 carbon atoms in the alkyl moiety. Especially preferred however is agmatine or 4-guanidino butylamine.

The key to the success of the present invention is the provision of a stable but readily cleavable bridging group between the guanidino moiety and the support phase It has been found that such a bridge may be readily provided by the sulfonyl phenoxy acetyl moiety In one embodiment of the synthesis, the primary amino group of agmatine is protected with a t-butoxy carbonylating agent, suitably ditert-butyl dicarbonate, by reaction preferably at ambient temperatures in the presence of a base, providing the protected material (V) which is then reacted in a similar solvent system with the aryl sulfonyl halide (VI) which may be a sulfonyl chloride or sulfonyl bromide. Where the ultimate synthetic sequences intended to follow the Boc protocol, the aromatic ring of the aryl sulfonyl halide is not substituted since such a situation will permit the use of trifluoroacetic acid as the intermediate deprotecting agent and hydrogen fluoride as the agent for final cleavage from the resin support phase. The thus obtained protected sulfonamido phenoxy acetic acid (VII) is then coupled to the support phase. In the preferred procedure, the coupling is carried out using any of the known dialkyl carbodiimide coupling procedures. For example, there may be utilized diisopropyl carbodiimide in the presence of 1-hydroxybenzenetriazole hydrate in dimethylformamide at ambient temperatures. Alternatively, there may be employed N,N'dicyclohexyl carbodiimide In this procedure the aforesaid Boc-sulfonamido phenoxy acetic acid (VII) is mixed with the carbo-diimide in 2 to 1 molar ratio N,N'dicyclohexyl urea is formed, removed by filtration and the resulting solution added to the support phase, suitably an amino methyl resin. It is preferred to carry out this reaction utilizing a ratio of resin amino component to Boc-amino acid to dicyclohexyl carbodiimide of 1:6:3.

In an alternate modification of the procedure, carboxy methoxy phenyl sulfonic acid is coupled with the amino methyl resin in accordance with the foregoing carbodiimide procedures, the sulfonic acid group of the product is converted to the corresponding sulfonyl chloride by reaction with thionyl chloride in dimethyl formamide and the resulting product coupled with the protected amino alkyl guanidine (V) in the presence of an organic base in a suitable organic solvent, for example, tetramethyl guanidine in chloroform, to yield the desired coupled product. As previously stated, if the protecting group is Boc, the aryl moiety of the sulfonamide bridge is unsubstituted However, where it is desired to proceed under the Fmoc protocol, it is desirable to substitute the aforesaid phenyl moiety with up to three methyl or methoxy groups since these weaken the sulfonamide group and enable it to be cleaved by trifluoro acetic acid.

In the third embodiment in place of utilizing Boc to protect the amino alkyl guanidine moiety, there is utilized N-benzyloxy carbonyl chloride in the presence of an aqueous alkali, suitably sodium hydroxide, preferably at about 4N under agitation and cooling to between about 5° and about 15° C. Upon acidification the protected product is precipitated and thereafter is reacted with the aryl sulfonyl chloride (XII) as previously. However, as stated above, in this case the aryl sulfonyl chloride (XII) should preferably carry between 1 and 3 substituents which may be alkyl or lower alkoxy, suitably methyl or methoxy. This reaction is carried out in the presence of a strong but dilute aqueous base, suitably about 1N sodium hydroxide. The reaction mixture is acidified and the product extracted, suitably with a water immiscible organic solvent such as ethyl acetate. The extract is then concentrated and hydrogenated, suitably at atmospheric pressure and temperature in the presence of a catalyst such as palladium on charcoal in a reduction inert solvent If ethyl acetate is used as the extractant, this may be used as the hydrogenation solvent. After removal of the Cbz group, the product (XIII) is reacted with Fmoc-Cl in the presence of a base to yield the corresponding Fmoc protected sulfonamido aryloxy acetic acid (XIV) which is then coupled to the support phase in the manner set forth hereinabove.

The peptides are synthesized by a suitable method, such as by exclusively solid-phase techniques, by partial solid-phase techniques, by fragment condensation or by classical solution phase synthesis. The employment of recently developed recombinant DNA techniques may be used to prepare a portion of an analog containing only natural amino acid residues. For example, the techniques of exclusively solid-phase synthesis are set forth in the textbook "Solid Phase Peptide Synthesis", J. M. Stewart and J. D. Young, Pierce Chem. Company, Rockford, Ill., 1984 (2nd. ed.), G. Barany and R. B. Merrifield, "The Peptides", Ch. 1, 1–285, pp. 1979, Academic Press, Inc., and M. Bodanszky, "Principles of Peptide Synthesis", Springer-Verlag, 1984. Classical solution synthesis is described in detail in the treatise "Methoden der Organischen Chemie (Houben-Weyl):

Synthese von Peptiden", E. Wunsch (editor) (1974) Georg Thieme Verlag, Stuttgart, W. Germany.

Common to such synthesis is the protection of the reactive side chain functional groups of the various amino acid moieties with suitable protecting groups which will prevent a chemical reaction from occurring at that site until the group is ultimately removed. Usually also common is the protection of an alpha-amino group on an amino acid or a fragment while that entity reacts at the carboxyl group, followed by the selective removal of the alpha-amino protecting groups to allow subsequent reaction to take place at that location. Accordingly, it is common that, as a step in the synthesis, an intermediate compound is produced which includes each of the amino acid residues located in its desired sequence in the peptide chain with side-chain protecting groups linked to the appropriate residues.

Also considered to be within the scope of the present invention are intermediates of the formula: [PR][PeP] attached to a support phase [SP] selected from the group consisting of amino resins and hydroxyl type resins, said combination having the structure

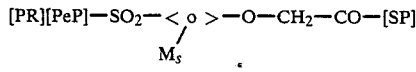

where M is hydrogen, lower alkyl or lower alkoxy of 1 to 5 carbon atoms, suitably methyl or methoxy, s is 0, 1, 2 or 3, [SP] is an amino or hydroxyl type resin, suitably [PR][PeP] has the structure

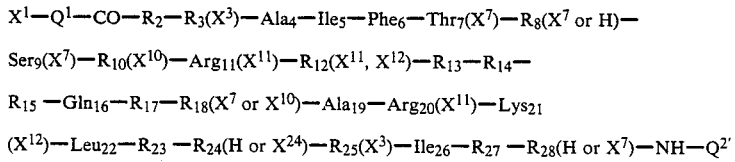

wherein: $X^1$ is either hydrogen or an alpha-amino protecting group. The alpha-amino protecting groups contemplated by $X^1$ are those well known to be useful in the art of step-wise synthesis of polypeptides. Among the classes of alpha-amino protecting groups which may be employed as $X^1$ are (1) aromatic urethan-type protecting groups, such as fluoroenylmethyloxycarbonyl (Fmoc), benzyloxycarbonyl (Cbz) and substituted Cbz, such as p-chlorobenzyloxycarbonyl, p-nitrobenzyloxycarbonyl, p-bromobenzyloxycarbonyl, and p-methoxybenzyloxycarbonyl; (2) aliphatic urethan protecting groups, such as t-butyloxycarbonyl (Boc), diisopropylmethyloxycarbonyl, allyloxycarbonyl; and (3) cycloalkyl urethan-type protecting groups, such as cyclopentyloxycarbonyl, adamantyloxycarbonyl, and cyclohexyloxycarbonyl. There are two preferred synthetic routes, one wherein the preferred alpha-amino protecting group is Boc; the other where said protecting group is Fmoc.

$X^3$ is a suitable ester-forming protecting group for the carboxyl group of Asp or Glu, such as benzyl (OBzl), 2,6-dichlorobenzyl, and t-butyl. In the Boc protocol, o-cyclohexyl and o-benzyl are preferred; in the Fmoc protocol t-butyl is preferred.

$X^7$ may be a suitable protecting group for the hydroxyl group of Thr or Ser, such as tert-butyl, Bzl, and 2,6-dichloro-benzyl. The preferred protecting in the Boc protocol is Bzl, and in the Fmoc protocol is tert-butyl.

$X^{10}$ may be a suitable protecting group for the phenolic hydroxyl group of Tyr, such as tert-butyl, Bzl, 4-Br-Cbz and 2,6-dichloro benzyl (DCB). The preferred protecting group in the Boc protocol is 2,6-dichlorobenzyl, and in the Fmoc protocol is tert-butyl.

$X^{11}$ is a suitable protecting group for the guanidino group of Arg, such as nitro, Tos, methyl-(t-butyl benzene)-sulfonyl, 4-methoxy-2,3,6-trimethylbenzenesulfonyl; in the Boc protocol Tos is the preferred group and 4-methoxy-2,3,6-trimethylbenzenesulfonyl in the Fmoc protocol.

$X^{12}$ is a suitable protecting group for the side chain amino group of Lys. Illustrative of suitable side chain amino protecting groups are 2-chlorobenzyloxycarbonyl (2-Cl-Z), Tos, t-amyloxycarbonyl and in the Boc protocol 2-chlorobenzyloxycarbonyl is the preferred protecting group and in the Fmoc protocol Boc is thus utilized.

$X^{24}$ is hydrogen or a protecting group for the imidazole nitrogen of His, such as Tos.

The selection of a side chain amino protecting group is not critical except that generally one is chosen which is not removed during deprotection of the alpha-amino groups during the synthesis In selecting a particular side chain protecting group to be used in the synthesis of the peptides, the following general rules are followed: (a) the protecting group preferably retains is protecting properties and is not split off under coupling conditions, (b) the protecting group should be stable to the reagent, is preferably stable under the reaction conditions selected for removing the alpha-amino protecting group at each step of the synthesis, and (c) the side chain protecting group must be removable, upon the completion of the synthesis containing the desired amino acid sequence, under reaction conditions that will not undesirably alter the peptide chain.

When the peptides are not prepared using recombinant DNA technology, they are preferably prepared using solid phase synthesis, such as that generally described by Merrifield, *J. Am. Chem. Soc.*, 85, p. 2149 (1963), although other equivalent chemical syntheses known in the art can also be used as previously mentioned.

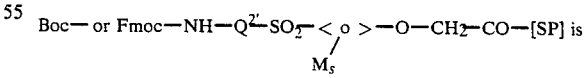

prepared as set forth above and constitutes the starting material for the synthetic sequence After removal of the alpha-amino protecting group, the remaining alpha-amino- and side chain-protected amino acids are coupled step-wise in the desired order to obtain the intermediate compound defined hereinbefore, or as an alternative to adding each amino acid separately in the synthesis, some of them may be coupled to one another prior to addition to the solid phase reactor. The selection of an appropriate coupling reagent is within the skill of the art. Particularly suitable as a coupling reagent is N,N'-diisopropyl carbodiimide (DIC).

The activating reagents used in the solid phase synthesis of the peptides are well known in the peptide art. Examples of suitable activating reactions are carbodiimides, such as N,N'-diisopropylcarbodiimide and N,N-dicyclohexyl carbodiimide (DCCI). Other activating reagents and their use in peptide coupling are described by M. Bodanszky, "Principles of Peptide Synthesis", Springer-Verlag, 1984.

Each protected amino acid or amino acid sequence is introduced into the solid phase reactor in about a threefold excess, and the coupling may be carried out in a medium or dimethylformamide (DMF): $CH_2Cl_2$ (1:1) or in DMF or $CH_2Cl_2$ alone. In cases where incomplete coupling occurs, the coupling procedure is repeated before removal of the alpha-amino protecting group prior to the coupling of the next amino acid The success of the coupling reaction at each stage of the synthesis, is preferably monitored by the ninhydrin reaction, as described by E. Kaiser, et al., *Anal. Biochem*, 34, 595 (1970).

After the desired amino acid sequence has been completed, the intermediate peptide can be removed from the resin support by treatment with a reagent such as liquid hydrogen fluoride or trifluoracetic acid, which not only cleaves the peptide from the resin but also cleaves all remaining side chain protecting groups $X^3$, $X^7$, $X^{10}$, $X^{11}$, $X^{12}$, and $X^{24}$ and the anchoring sulfonamido bond and also the alpha-amino protecting group $X^1$. As indicated above these groups have different values depending on whether Boc or Fmoc protocols are used, to obtain the peptide in the form of the free acid. If Met is present in the sequence, the Boc protecting group is preferably first removed using trifluoroacetic acid (TFA)/ethanedithiol prior to cleaving the peptide from the resin with HF to eliminate potential S-alkylation. When using hydrogen fluoride for cleaving, anisole and methylethyl sulfide are included as scavengers in the reaction vessel.

The following Examples set forth a preferred method for synthesizing peptides by the solid-phase technique

EXAMPLE I

Synthesis of Boc-Agmatine (V)

Agmatine sulfate (2.28 g, 10 mmole) was suspended in water (10 ml) and triethylamine (2.8 ml, 20 mmole) was added. Thereafter the solution thus obtained was diluted with dioxan (10 ml) and di-tert-butyl dicarbonate (2.4 ml, 10 mmole) added to the mixture with stirring on ice bath (cooling on ice). The mixture was then allowed to warm to ambient temperature. After 5 hours, second portions of triethylamine (1.4 ml, 10 mmole) and di-tert-butyl di-carbonate (1.2 ml. 5 mmole) were added while stirring was continued at ambient temperature overnight. The mixture was filtered and evaporated under reduced pressure. The residue was dissolved in chloroform (50 ml), the solution was dried over sodium sulfate and concentrated under reduced pressure to an oil which was crystallized from chloroform/acetone. Boc-agmatine separated as a triethylamine-sulfate-salt. Yield 3.25 g (75%); m.p. 60°–65° C.; Analysis: Calculated for $(C_{10}H_{22}O_2N_4)$ $(C_6H_{15}N)$ $(H_2SO_4)$; C=44.73%, H=9.15%, N=16.30%, S=7.46%. Found C=44.8%, H=9.2%, N=16.2%, S=7.5%.

TLC: Sigma $F_{254}$ anal. plate, detection UV 254 nm, 355 nm and Sakaguchi-reagent (indicating the guanidino moiety) Solvent system: Ethyl acetate-Pyridine-Acetic acid-Water (60; 20:6:11)

| | |
|---|---|
| $R_f$ N-Boc-Agmatine | 0.43 |
| $R_f$ Agmatine | 0.00 |

EXAMPLE II

Synthesis of 4-Chlorosulfonyl Phenoxyacetic Acid 50 mM (7, 6 g) phenoxyacetic acid was dissolved in 75 ml chloroform, cooled in ice-bath and stirred 16.5 ml chlorosulfonic acid in 25 ml chloroform was added dropwise during a period of 10–15 minutes. The temperature was kept at 0° for 20 minutes then allowed to remain at room temperature for an additional 30 minutes. The two-phase liquid was poured into a beaker containing about 300 g. of crushed ice. The separated aqueous phase was extracted twice with 50 ml ether, then the combined organic phase was dried over anhydrous sodium sulfate. The solvent was removed in vacuo and the remaining material was recrystallized from ether-hexane mixture. Yield 9.75 g. (77.8%, Melting point 155°–157° (uncorrected).

TLC: Sigma $F_{254}$ anal. plate. Detection: UV 254 nm, 355 10 nm.

Eluent (A) Ethyl Acetate-Acetic acid 9:1 v/v

Eluent (B) Ether-Hexane 2:1 v/v plus one drop of acetic acid in 10 ml of eluent.

| |
|---|
| $R_f$ Phenoxyacetic Acid, System A: 0.85 |
| System B: 0.34 |
| $R_f$ 4-Chlorosulfonyl Phenoxyacetic Acid, System A: 0.77 |
| System B: 0.17 |

In accordance with the above procedure but utilizing, in place of phenoxy acetic acid, 2,3,5-trimethyl phenoxy acetic acid and 2,3,6-trimethyl phenoxy acetic acid, there are obtained the corresponding 4-chlorosulfonyl-2,3,5-trimethyl phenoxy acetic acid ($R_f$ values: 0.78 and 0.75, respectively, in a 8:4:0.05 (v/v) mixture of ether-hexane-acetic acid on Sigma $F_{254}$ TLC plate).

EXAMPLE III

Boc-Agmatine-[SPA] (VII)

Boc-Agmatine (4.29 g, 10 mmole) is taken up in a mixture of acetone (50 ml) and 1N sodium hydroxide (50 ml) with stirring and cooling in an ice bath and 4-chlorosulfonyl phenoxyacetic acid (3.8 g, 15 mmole) added to the solution. Stirring is continued for 3 hours and the pH of the reaction mixture is kept at 11–12 by adding 4N sodium hydroxide. The reaction mixture is acidified with 10% citric acid solution and concentrated under reduced pressure to the half of its volume, and extracted with ethyl acetate (3×50 ml). The combined extracts are washed with saturated sodium chloride solution, dried over sodium sulfate, and evaporated under reduced pressure. Boc-agmatine-sulfonyl-phenoxyacetic acid (abbreviated as Boc-agmatine-[SPA]) is obtained as thick oil (3.6 g, 81%). $R_f$=0.5 in a 9:1 mixture (v/v) of ethyl acetate-acetic acid on Sigma $F_{254}$ TLC plate.

In accordance with the foregoing procedure but where, in place of Boc-agmatine, there is used Cbz-agmatine and in place of 4-chlorosulfonyl phenoxy acetic acid, there is utilized 4-chlorosulfonyl-2,3,5- trimethyl phenoxy acetic acid or 4-chloro-sulfonyl 2,3,6-trimethyl phenoxy acetic acid, there is obtained the corresponding Cbz-agmatine-2,3,5-trimethyl-[SPA] and Cbz-agmatine-2,3,6-trimethyl-[SPA].

EXAMPLE IV

Coupling of Boc-Agmatine (SPA) to Support Phase 3.11 g (7 mM) Boc-Agmatine-(SPA) in 50 ml DMF was reacted with 1.89 g (14 mM) HOBt and 1.1 ml (7 mM) DIC at room temperature for 30 minutes, and the resulted active ester solution in this way was added to 5 g. aminomethyl-resin (0.7 m. equiv./g. capacity) which was swollen in dichloro-methane, deprotonated in 10% diisopropyl ethylamine chloroform mixture and washed twice with DMF. The reaction was complete for 90 minutes, tested by ninhydrin-reaction. Finally, the coupled resin was washed with DMF, dichloromethane and DMF again.

EXAMPLE V

Synthesis of Cbz-Agmatine

Agmatine sulfate (2.28 g, 10 mM)·and sodium 5 hydrogencarbonate (2.52 g, 30 mM) was dissolved in a mixture of 20 ml water and 20 ml dioxane. The mixed solution was cooled on ice bath and benzyloxycarbonylchloride (1.85 ml, 13 mM) in 10 ml dioxane was added dropwise during a period of 15 minutes. The stirring was continued at 0° C. for 1 hour and overnight at room temperature. The reaction mixture was evaporated to dryness, the remaining solid material was agitated with $2\times50$ ml chloroform and after filtration, the solution was evaporated under reduced pressure The oily compound was used without further purification.

$R_f$: 0.66 in mixture of Ethyl acetate-Pyridine-Acetic Acid-Water 45:20:6:11 (v/v) on Sigma $F_{254}$ TLC plate. Detection: under UV light, Sakaguchi reagent

EXAMPLE VI

Synthesis of Agmatine-sulfonyl-2,3,5(and 2,3,6)-Trimethylphenoxy acetic acids

Cbz-agmatine (2.85 g, 10 mM) and 4-chlorosulfonyl-2, 3,5-trimethylphenoxy acetic acid (or 4-chlorosulfonyl-2,3, 6-trimethylphenoxy acetic acid (4.39 g, 15 mM) were reacted as described in Example III. Cbz-agmatine-sulfonyl-2,3,5 (or 2,3,6)-trimethylphenoxy acetic acid obtained was dissolved in ethanol (50 ml) and hydrogenated over palladium-charcoal catalyst (0.5 g). The catalyst was filtered off and the solvent was removed under reduced pressure. The residue was crystallized from an ethanol-water mixture to yield agmatine-sulfonyl-2,3,6-trimethylphenoxy acetic acid (2.70 g. 70% and 2.78 g. 72%, respectively).

$R_f$ values for both compounds were the same, 0.28 in a 4:1:1 (v.v) mixture of n-butanol-acetic acid-water on Sigma $F_{254}$ TLC plate.

EXAMPLE VII

Coupling of Fmoc-Agmatine-sulfonyl-2,3,5 (and 2,3,6)-trimethylphenoxy acetic acid to Support Phase Agmatine-sulfonyl-2,3,5 (or 2,3,6)-trimethylphenoxyacetic acid (2.70 g, 7 mM) was dissolved in a 10% solution of sodium carbonate (18.6 ml) and dioxane (11 ml) added. The solution was stirred and cooled in an ice-water bath, then 9-fluorenylmethyl chlorocarbonate (1.82 g, 7 mM) was added in small portions. The stirring was continued at ice-bath temperature for 4 hours and then at room temperature for a further 8 hours. The mixture was poured into 400 ml water and extracted with $2\times100$ ml ether. The aqueous phase was acidified with 1:1 hydrochloric acid solution and extracted $3\times100$ ml ethyl acetate. After drying over anhydrous sodium sulfate the solvent was removed under reduced pressure. The Fmoc-Agmatine-sulfonyl-2,3,5 (or 2,3,6)-trimethylphenoxy acetic acid obtained was dissolved in DMF (50 ml) and coupled to 5 g. aminomethyl resin as described in Example IV.

In accordance with the foregoing procedures, but where, in place of amino methyl resins there are utilized benzhydrylamine, p-methylbenzhydrylamine and p-alkoxy benzyl alcohol resins (presence of a catalytic amount of p-dimethylamino pyridine is necessary), similar coupled products are obtained.

EXAMPLE VIII

The synthesis of an hpGRH analog of the formula:

3-(4-hydroxyphenyl)propionyl-D—Ala$_2$—Asp$_3$—Ala$_4$—Ile$_5$—Phe$_6$—

Thr$_7$—Asn$_8$—Ser$_9$—Tyr$_{10}$—Arg$_{11}$—Lys$_{12}$—Val$_{13}$—Leu$_{14}$—Gly$_{15}$—Gln$_{16}$—

Leu$_{17}$—Ser$_{18}$—Ala$_{19}$—Arg$_{20}$—Lys$_{21}$—Leu$_{22}$—Leu$_{23}$—Gln$_{24}$—Asp$_{25}$ —

Ile$_{26}$—Nle$_{27}$—Ser$_{28}$—NH—(CH$_2$)$_4$—NH.C.(NH).NH$_2$ was carried out in a stepwise manner on a Beckman 990 synthesiser starting with the appropriate Boc—NH—(CH$_2$)$_4$—NH.C.(NH)—NH—SO$_2$-<o>-OCH$_2$—CO—[SP] in acordance with the procedures set forth below.

(a) deblocking and build-up.

Deblocking is carried out in accordance with Schedule A as follows:

| SCHEDULE A | |
|---|---|
| Reagent | Mixing Time (mins) |
| 1. TFA/Toluene 1:2* | 2 |
| 2. TFA/Toluene 1:2* | 28 |
| 3. CH$_2$Cl$_2$ | 2 |
| 4. MeOH | 2 |
| 5. CH$_2$Cl$_2$ | 2 & 2 |
| 6. DIEA (10%) in CH$_2$Cl$_2$ | 2 & 8 |
| 7. MeOH | 2 |
| 8. CH$_2$Cl$_2$ | 2 |

Coupling is carried out in accordance with Schedule B as follows:

| SCHEDULE B | |
|---|---|
| Reagent | Mixing Time (mins) |
| 9A. DIC (2 eq) + HOBt (4 eq) | — |
| 10A. Boc Amino Acid (2 eq) # | 60–90 |
| or | |
| 9B. DIC (2 eq) + | — |

SCHEDULE B -continued

| Reagent | Mixing Time (mins) |
|---|---|
| 10A. Boc Amino Acid (4 eq) @ | 60-90 |
| 11A. DMF | 2 |
| or | |
| 11B. CH$_2$Cl$_2$ | 2 |
| 12. CH$_2$Cl$_2$ | 2 & 2 |

Briefly, 1 to 2 mmol. of Boc-protected amino acid in DMF is used per gram of resin. When Boc-Arg (Tos) is being coupled, a mixture of 50% DMF and methylene chloride is used. Bzl ether is used as the hydroxyl side-chain protecting group for Ser and Thr. 2-Chloro benzyloxycarbonyl (2Cl-Cbz) is used as the protecting group for the Lys side chain. Tos is used to protect the guanidino group of Arg and the Glu and Asp side-chain carboxyl group is protected with OBzl or OChx. The phenolic hydroxyl group of Tyr is protected with 2,6-dichlorobenzyl (DCB). The following compound is obtained:

3-(4-hydroxyphenyl)propionyl-D—Ala$_2$—Asp$_3$(X$^3$)—Ala$_4$—Ile$_5$

—Phe$_6$—Thr$_7$(X$^7$)—Asn$_8$—Ser$_9$(X$^7$)—Try$_{10}$(X$^{10}$)—Arg$_{11}$(X$^{11}$)—

Lys$_{12}$(X$^{12}$)—Val$_{13}$—Leu$_{14}$—Gly$_{15}$—Gln$_{16}$—Leu$_{17}$—Ser$_{18}$(X$^7$)—Ala$_{19}$—

Arg$_{20}$(X$^{11}$)—Lys$_{21}$(X$^{12}$)—Leu$_{22}$—Leu$_{23}$—Gln$_{24}$—Asp$_{25}$(X$^3$)—Ile$_{26}$

—Nle$_{27}$—Ser$_{28}$(X$^7$)—NH—(CH$_2$)$_4$—NH.C.(NH).NH.SO$_2$—< o >(M$_s$)—OCH$_2$—

CO—[SP] wherein X$^3$ is O— cyclohexylester, X$^7$ is O—benzyl ether, X$^{10}$ is O-2,6-ClBz ether, X$^{11}$ is tosyl, X$^{12}$ is 2-Cbz, (b) Cleavage and deprotection
(The procedure followed is substantially that of Tam et al J. Amer. Chem. Soc. 105, 6442, (1983))

The protected peptide produced as above is utilized as starting material.

The protected peptide is treated with TFA-Toluene (1:2 v/v), prior to the HF treatment, using two treatments with (2+28 min. then washed 3× with CH$_2$Cl$_2$.

The incomplete mixing of the HF reagent and the peptidyl resin or peptide can be alleviated simply by the following order of addition of the reagents: (a) peptide or peptidyl-resin, (b) p-cresol, p-thiocresol, or both, in a melted form, carefully on top of the resin by a warm peptide, (c) after cooling and the p-cresol mixture has solidified, magnetic stirring bar, and (d) dimethyl sulfide.

(a) Low Concentration HF Step.

The reagents (dimethyl sulfide, 6,5 ml.; p-cresol, 0.75 ml.; p-thiocresol, 0.25 ml.), total volume 7,5 ml, and peptide-resin (1.0 g.) were placed in the reaction vessel and connected to the HF line The vessel was cooled to ≔78° C. for 0.5 hours (longer cooling time for large volume of reagent). The line was evacuated briefly for 0.5 min. and HF was quickly distilled into the evacuated reaction vessel to a 10 ml mark (or any desired volume). The reaction was then quickly equilibrated to 0° C. by ice bath and allowed to stir vigorously for 2 hours (check stirring constantly). The HF-dimethyl sulfide-p-cresol mixture at this point was colorless to light yellow. After 2 hours, the mixture was then evacuated first with water aspirator (caution:bumping) with the valve of the reaction to the aspirator only partially opened After most of the reagent was removed, the mixture was further evacuated by mechanical pump to a light colored liquid (usually at about 0.5 ml mark).

(b) High Concentration HF Step

The evaporated reaction vessel from the previous low concentration step, was cooled again to −78° C., evacuated, and charged again with HF to the 10 ml volume mark. [Note: if the removal of HF and dimethyl sulfide after the first stage was incomplete, recharging HF to 5 ml will result in a final HF concentration that is less than 90%. Under such circumstances the more acid-resistant resins, such as benzhydrylamine-resin, or peptides with many acid-resistant protecting groups, such as tosyl or 2,6-dichlorobenzyl, will not be completely deprotected. If there is doubt about the completion of the evaporation step, HF should be charged to 7.5 or 10 ml total volume, so that the final HF concentration will be certain to 1 reach at least 90% by volume. A final mixture of 95% HF and 5% cresol plus thiocresol has been found to be entirely satisfactory.] The reaction was then equilibrated to 0° C. and allowed to react for 45-60 minutes. The HF was then removed as described previously.

After the cleavage process the remaining solid mass was mixed with ether several times to remove the apolar additives and apolar side products together with the contaminated traces of HF. The crude peptides were extracted from bedside the resin particles with 10% of acetic acid water mixture, then liophilized.

The crude peptides were purified by HPLC method using semipreparative or preparative reverse-phase chromatographic columns, (Vydac C18, 10×250 mm, particle size 5 micron or Dynamax C18 Macro HPLC column 21, 4×250 mm, particle size 12 micron).

Pumps: Beckman 114M Solvent Delivery Module
Detector Beckman 160A Absorbance Detector
Gradient Controller Beckman 420 Grad Cont.
Injector: Altex 210A
Detection Wavelength 214 mm
Eluents:
A, 0.1% TFA in water (high purity)
B, 0.1% TFA in water-acetonitile 3:7 (by vol ) mixture.

EXAMPLE IX

The synthesis of an hpGRH analog of the formula:

3-(4-hydroxyphenyl)propionyl-D—N—Me—Ala$_2$—Asp$_3$—Ala$_4$—Ile$_5$—

Phe$_6$—Thr$_7$—Asn$_8$—Ser$_9$—Tyr$_{10}$—Arg$_{11}$—Lys$_{12}$—Val$_{13}$—Leu$_{14}$—Gly$_{15}$

Gln$_{16}$—Leu$_{17}$—Ser$_{18}$—Ala$_{19}$—Arg$_{20}$—Lys$_{21}$—Leu$_{22}$—Leu$_{23}$—Gln$_{24}$—

$Asp_{25}-Ile_{26}-Nle_{27}-Ser_{28}-NH-(CH_2)_4-NH.C.(NH).NH_2$ was carried out in a stepwise manner on a Beckman 990 synthesiser starting with the appropriate Fmoc-NH-$(CH_2)_4$—NH.C.(NH).NH—$SO_2$—<o>$(M_2)$—OCH-$_2$—CO—[SP] in accordance with the procedures set forth below.

(a) deblocking and build-up.

Deblocking is carried out in accordance with Schedule A as follows:

SCHEDULE A

| Reagent | Mixing Time (mins) |
|---|---|
| 1. Piperidine/DMF 1:4* | 3 |
| 2. Piperidine/DMF 1:4* | 7 |
| 3. DMF | 2 |
| 4. MeOH | 2 |
| 5. $CH_2Cl_2$ | 2 & 2 |
| 6. DMF | |
| 7. DMF | 2 |

Coupling is carried out in accordance with Schedule B as follows:

SCHEDULE B

| Reagent | | Mixing Time (mins) |
|---|---|---|
| 8A. | DIC (2 eq) + HOBt (4 eq) | — |
| 9A. | Fmoc Amino Acid (2 eq) # | 60-90 |
| or | | |
| 8B. | DIC (2 eq) + | — |
| 9A. | Fmoc Amino Acid (4 eq) @ | 60-90 |
| 10A. | DMF | 2 |
| or | | |
| 10B. | $CH_2Cl_2$ (twice) | 2 |
| 11. | $CH_2Cl_2$ | 2 & 2 |

Briefly, 1 to 2 mmol. of Fmoc-protected amino acid in DMF is used per gram of resin. When Fmoc-Arg (4-MeO-2,3,6-tribenzene sulfonyl) is being coupled, a mixture of 50% DMF and methylene chloride is used. T-Butyl ether is used as the hydroxyl side-chain protecting group for Ser 25 and Thr. Tert-butyloxycarbonyl (Boc) is used as the protecting group for the Lys side chain 4-MeO-2,3,6tribenzene sulfonyl is used to protect the guanidino group of Arg and the Glu and Asp side-chain carboxyl group protected with t-butyl ester. The phenolic hydroxyl group of Tyr is similarly protected with t-butyl ether. The following compound is thus obtained:

3-(4-hydroxyphenyl propionyl)-D—N—Me—$Ala_2$—$Asp_3(X^3)$—$Ala_4$—

$Ile_5$—$Phe_6$—$Thr_7(X^7)$—$Asn_8(x^7)$—$Ser_9(X^7)$—$Tyr_{10}(X^{10})$—$Arg_{11}$ $(X^{11})$—$Lys_{12}(X^{12})$—$Val_{13}$—$Leu_{14}$—$Gly_{15}$—$Gln_{16}$—$Leu_{17}$—$Ser_{18}(X^7)$—

$Ala_{19}$—$Arg_{20}(X^{11})$—$Lys_{21}(X^{12})$—$Leu_{22}$—$Leu_{23}$—$Gln_{24}$—$Asp_{25}(X^3)$—

$Ile_{26}$—$Nle_{27}$—$Ser_{28}(X^7)$—NH—$(CH_2)_4$—NH.C.(NH).NH.$SO_2$—<o>$(M_s)$—

$OCH_2$—CO—[SP]

wherein $X^3$ is O-Butyl ether, $X^7$ is O-butyl ether, $X^{10}$ is O-butyl ether, $X^{11}$ is 4-methoxy-2,3,6-trimethylbenzylsulfonyl and $X^{12}$ is Boc.

(b) Cleavage and deprotection

The protected peptide produced as above is utilized as starting material. The cleavage of the peptide from the solid support and the removal of side chain protecting groups was carried out simultaneously by the reaction of the protected peptide resin with TFA-thioanisole (5%) at a temperature 25°–30° C. for 2–3 hours (10 ml of liquid per each gram of resin was used). After the completion of the reaction the reagent was removed in vacuo at room temperature. The remaining material was extracted, first with ether (removing the nonpolar side-products), then the crude peptide was extracted from the filtered-cake with 10% acetic acid and the filtrate was lyophilized.

EXAMPLE X

The synthesis of an hpGRH analog of the formula:

H—Tyr—D—N-Methyl-$Ala_2$—$Asp_3$—$Ala_4$—$Ile_5$—$Phe_6$—$Thr_7$—$Asn_8$—$Ser_9$—

$Tyr^{10}$—$Arg_{11}$—$Lys_{12}$—$Val_{13}$—$Leu_{14}$—$Gly_{15}$—$Gln_{16}$—$Leu_{17}$—$Ser_{18}$—

$Ala^{19}$—$Arg_{20}$—$Lys_{21}$—$Leu_{22}$—$Leu_{23}$—$Gln_{24}$—$Asp_{25}$—$Ile_{26}$—$Nle_{27}$—

$Ser^{28}$—NH—$(CH_2)_4$—NH.C.(NH).$NH_2$ was carried out in a stepwise manner on a Beckman 990 synthesizer starting with the appropriate Boc-NH-$(CH_2)_4$-NH.C.(NH).NH-$SO_2$-<o>$(M_s)$-$OCH_2$-CO-[SP] in accordance with the procedures of Example VIII. The sample was judged substantially pure using TLC and HPLC.

EXAMPLE XI

The synthesis of an hpGRH analog of the formula:

DL-3-(4-hydroxyphenyl)lactoyl-D—Ala$_2$—Asp$_3$—Ala$_4$—Ile$_5$—Phe$_6$

—Thr$_7$—Asn$_8$—Ser$_9$—Tyr$_{10}$—Arg$_{11}$—Lys$_{12}$—Val$_{13}$—Leu$_{14}$—Gly$_{15}$—Gln$_{16}$

—Leu$_{17}$—Ser$_{18}$—Ala$_{19}$—Arg$_{20}$—Lys$_{21}$—Leu$_{22}$—Leu$_{23}$—Gln$_{24}$—Asp$_{25}$—

Ile$_{26}$—Nle$_{27}$—Ser$_{28}$ was carried out in a stepwise manner on a Beckman 990 synthesizer starting with the appropriate Boc- or Fmoc-NH—(CH$_2$)$_4$—NH—C(NH)—NH—SO$_2$—<o>(M-s)—OCH$_2$—CO-[SP] in accordance with the procedures of Example VIII or IX. The sample was judged substantially pure using TLC and HPLC.

EXAMPLE XII

The synthesis of an hpGRH analog of the formula:

H—His—D—Ala$_2$—Asp$_3$—Ala$_4$—Ile$_5$—Phe$_6$—Thr$_7$—Asn$_8$—Ser$_9$—Tyr$_{10}$—

Arg$_{11}$—Lys$_{12}$—Val$_{13}$—Leu$_{14}$—Gly$_{15}$—Gln$_{16}$—Leu$_{17}$—Ser$_{18}$—Ala$_{19}$—

Arg$_{20}$—Lys$_{21}$—Leu$_{22}$—Leu$_{23}$—Gln$_{24}$—Asp$_{25}$—Ile$_{26}$—Nle$_{27}$—Ser$_{28}$—NH

—(CH$_2$)$_4$—NH.C.(NH).NH$_2$ was carried out in a stepwise manner on a Beckman 990 synthesiser starting with the appropriate Boc— or Fmoc—NH—(CH$_2$)$_4$—NH.C.(NH).NH—SO$_2$—<o>(M-s)—OCH$_2$—CO—[SP] in accordance with the procedures of Example VIII or IX. The same was judged substantially pure using TLC and HPLC

EXAMPLE XIII

The synthesiser of an hpGRH analog of the formula:

H—D—Tyr—D—N-Methyl-Ala$_2$—Asp$_3$—Ala$_4$—Ile$_5$—Phe$_6$—Thr$_7$—Asn$_8$—

Ser$_9$—Tyr$_{10}$—Arg$_{11}$—Lys$_{12}$—Val$_{13}$—Leu$_{14}$—Gly$_{15}$—Gln$_{16}$—Leu$_{17}$—

Ser$_{10}$—Ala$_{19}$—Arg$_{20}$—Lys$_{21}$—Leu$_{22}$—Leu$_{23}$—Gln$_{24}$—Asp$_{25}$—Ile$_{26}$—

Nle$_{27}$—Ser$_{28}$—NH—(CH$_2$)$_4$—NH.C.(NH).NH$_2$ was carried out in a stepwise manner on a Beckman 990 synthesiser starting with the appropriate Boc— or Fmoc—NH—(CH$_2$)$_4$—NH.C.(NH).NH—SO$_2$—<o>(M-s)—OCH$_2$—CO—[SP] in accordance with the procedures of Example VIII or IX. The sample was judged substantially pure using TLC and HPLC.

EXAMPLE XIV

The synthesis of an hpGRH analog of the formula:

H—D—Tyr—D—Ala$_2$—Asp$_3$—Ala$_4$—Ile$_5$—Phe$_6$—Thr$_7$—Asn$_8$—Ser$_9$—Tyr$_{10}$

—Arg$_{11}$—Lys$_{12}$—Val$_{13}$—Leu$_{14}$—Gly$_{15}$—Gln$_{16}$—Leu$_{17}$—Ser$_{18}$—Ala$_{19}$—

Arg$_{20}$—Lys$_{21}$—Leu$_{22}$—Leu$_{23}$—Gln$_{24}$—Asp$_{25}$—Ile$_{26}$—Nle$_{27}$—Ser$_{28}$—NH

—(CH$_2$)$_4$—NH.C.(NH).NH$_2$ was carried out in a stepwise manner on a Beckman 990 synthesiser starting with the appropriate Boc— or Fmoc—NH—(CH$_2$)$_4$—NH.C.(NH).NH—SO$_2$<o>(M-s)—OCH$_2$—CO—[SP] in accordance with the proceudures of Example VIII or IX. The sample was judged substantially pure using TLC and HPLC.

EXAMPLE XV

The synthesiser of an hpGRH analog of the formula:

H—Tyr—D—Ala$_2$—Asp$_3$—Ala$_4$—Ile$_5$—Phe$_6$—Thr$_7$—Asn$_8$—Ser$_9$—Tyr$_{10}$—

Arg$_{11}$—Lys$_{12}$—Val$_{13}$—Leu$_{14}$—Gly$_{15}$—Gln$_{16}$—Leu$_{17}$—Ser$_{18}$—Ala$_{19}$—

Arg$_{20}$—Lys$_{21}$—Leu$_{22}$—Leu$_{23}$—Gln$_{24}$—Asp$_{25}$—Ile$_{26}$—Nle$_{27}$—Ser$_{28}$—NH

—(CH$_2$)$_4$—NH.C.(NH).NH$_2$ was carried out in a stepwise manner on a Beckman 990 synthesiser starting with the appropriate Boc— or Fmoc—NH—(CH$_2$)$_4$—NH.C.(NH).NH—SO$_2$—<o>(M-s)—OCH$_2$—CO—[SP] in accordance with the procedures of Example VIII or IX. The sample was judged substantially pure using TLC and HPLC.

EXAMPLE XVI

The synthesis of an hpGRH analog of the formula:

(p-hydroxyphenyl)pyruvoyl-D—Ala$_2$—Asp$_3$—Ala$_4$—Ile$_5$—Phe$_6$—

Thr$_7$—Asn$_8$—Ser$_9$—Tyr$_{10}$—Arg$_{11}$—Lys$_{12}$—Val$_{13}$—Leu$_{14}$—Gly$_{15}$—Gln$_{16}$—

-continued $Leu_{17}$—$Ser_{18}$—$Ala_{19}$—$Arg_{20}$—$Lys_{21}$—$Leu_{22}$—$Leu_{23}$—$Gln_{24}$—$Asp_{25}$—

$Ile_{26}$—$Nle_{27}$—$Ser_{28}$—$NH$—$(CH_2)_4$—$NH.C.(NH).NH_2$ was carried out in a stepwise manner on a Beckman 990 synthesiser starting with the appropriate Boc— or Fmoc—$NH$—$(CH_2)_4$—$NH.C.(NH).NH_2SO_2$—<o>(M-$_s$)—$OCH_2$—$CO$—[SP] in accordance with the procedures of Example VIII or IX. The sample was judged substantially pure using TLC and HPLC.

EXAMPLE XVII

The synthesis of an hpGRH analog of the formula:

4-hydroxyphenylacetyl-D—$Ala_2$—$Asp_3$—$Ala_4$—$Ile_5$—$Phe_6$—

$Thr_7$—$Asn_8$—$Ser_9$—$Tyr_{10}$—$Arg_{11}$—$Lys_{12}$—$Val_{13}$—$Leu_{14}$—$Gly_{15}$—$Gln_{16}$—

$Leu_{17}$—$Ser_{18}$—$Ala_{19}$—$Arg_{20}$—$Lys_{21}$—$Leu_{22}$—$Leu_{23}$—$Gln_{24}$—$Asp_{25}$—

$Ile_{26}$—$Nle_{27}$—$Ser_{28}$ was carried out in a stepwise manner on a Beckman 990 synthesizer starting with the appropriate Boc— or Fmoc—$NH$—$(CH_2)_4$—$NH$—$C(NH)$—$NH$—$SO_2$—<o>($M_s$)—$O$—$CH_2$—$CO$—[SP] in accordance with the procedures of Example VIII or XI. The sample was judged substantially pure using TLC and HPLC.

EXAMPLE XVIII

The synthesis of an hpGRH analog of the formula:

3-hydroxyphenylacetyl-D—$Ala_2$—$Asp_3$—$Ala_4$—$Ile_5$—$Phe_6$—

$Thr_7$—$Asn_8$—$Ser_9$—$Tyr_{10}$—$Arg_{11}$—$Lys_{12}$—$Val_{13}$—$Leu_{14}$—$Gly_{15}$—$Gln_{16}$—

$Leu_{17}$—$Ser_{18}$—$Ala_{19}$—$Arg_{20}$—$Lys_{21}$—$Leu_{22}$—$Leu_{23}$—$Gln_{24}$—$Asp_{25}$—

$Ile_{26}$—$Nle_{27}$—$Ser_{28}$ was carried out in a stepwise manner on a Beckman 990 synthesiser starting with the appropriate Boc— or Fmoc—$NH$—$(CH_2)$—$NH$—$C(NH)$—$SO_2$—<o>(M-$_s$)—$O$—$CH_2$—$CO$—[SP] in accordance with the procedures of Example VIII or IX. The sample was judged substantially pure using TLC and HPLC.

EXAMPLE XIX

In accordance with the procedures of Example XVI, but wherein place of (p-hydroxylphenyl)pyruvoyl the terminal moiety is
3-amino-$Tyr_1$-,
3,5-diamino-$Tyr_1$-,
N-acetyl-3,5-diamino-$Tyr_1$-,
D-$Tyr_0$, $Gly_1$-,
D-$Tyr_0$, -$Ala_1$-,
D-$Tyr_0$, $GABA_1$-,
2-hydroxyphenyl-acetyl-,
4-hydroxybenzoyl,
4-hydroxylphenylglycine
4-hydroxycinnamyl-,
3,4-dihydroxyphenyl-acetyl-,
3,4-dihydroxycinnamyl-,
3,4-dihydroxy-hydrocinnamyl-,
S-Tritylmercaptopropionyl-$Tyr_1$-,
S-mercaptopropionyl-$Tyr_1$- or S-Tritylmercaptopropionyl-D-Tyr there is obtained the corresponding oligopeptide.

Test Procedures

The compounds of the present invention were tested both in vitro in rat cell culture and in vivo in rats to determine GHRH activity. The protocols are as follows:

EXAMPLE XX

Preparation of Cells

Twenty-four adult male or female Sprague-Dawley strain rats were decapitated for each experiment. After posterior lobes were removed, the anterior pituitaries were cut into small pieces and incubated in a Dubnoff incubator for 45 minutes at 37° C. in 10 ml. of oxygenated Medium 199 (GIBCO) containing 0.5% collagenase (Sigma Type 1), 0.25% bovine serum albumin (BSA) (Sigma RIA grade), and 5 μg./ml. Gentamicin Sulphate (Sigma). After this incubation, there were no apparent changes in the appearance of the tissue. However, the fragments could be easily dipsersed into single cells by repeated suction and expulsion from a Gilson Pipetman. After 30 to 60 Pipetman operations, the tissue fell apart; a second collagenase incubation was not usually necessary. The cell suspension was centrifuged at room temperature for 10 minutes at 10033 g. The cell pellet was then resuspended in 1.0 ml. of medium. A small aliquot was diluted for counting the cells, and the rest or one suspension was divided into 2 equal volumes. Each volume (containing about $5 \times 10^6$ cells, usually between 3.5 and $7.0 \times 10^6$) was mixed with 0.5 ml. Sephadex G-15 which had been equilibrated with previously oxygenated medium. The mixture of pituitary cells and Sephadex was transferred into 2 chambers of the superfusion apparatus and perfused with the medium. The medium was always freshly prepared in a way similar to that used for the enzymatic dispersion, but with the omission of the collagenase, passed through a millipore filter, and gassed continuously with a mixture of $O_2$ (95%) and $CO_2$ (5%) during the experiment.

Superfusion Apparatus

The superfusion apparatus (FIG. 1) consisted of a number of 1 ml. plastic syringe barrels (modified by cutting off their distal end) and mounted vertically in a Plexiglas holder which was kept at 37° C. by circulating water. The unit was constructed in our laboratory workshop. Properly greased O-rings prevented the leakage of the circulating water around the syringe barrels. Each barrel was fitted with plungers at both ends. Holes were drilled in the plungers to accommodate plastic tubing. The lower plunger was covered with a small piece of 30 μm-pore nylon net to keep the Sephadex beads from escaping. The "pores" between the beads were small enough to prevent the pituitary cells from escaping and large enough to allow a practically unrestricted flow of medium through the cell column. The upper plunger tubing was used for directing the flow through the chamber from the medium reservoir. The flow through the system (0.5 ml min) was controlled with a multichannel peristaltic pump (Gilson) Minipulse type HP-8 which was placed after the superfusion chamber; the tubing of the lower plunger was connected to the pump and from there to a four-channel fraction collector (a modified Gilson type Anacol SC30). Thus, the system was operated with a negative pressure in order to get fewer fluctuations in the flow rate. The medium from the chamber was collected into disposable borosilicate glass tubes containing 30 μl of 1N HCl for immediate acidifying of the perfusate to prevent the loss of ACTH activity at neutral or alkaline pH (14, 34, 38).

Radioimmunoassays

ACTH radioimmunoassays were performed on 100 μl aliquots of undiluted superfusion medium essentially as described elsewhere (14); however, the separation of bound and free ACTH was accomplished by a polyethylene glycol facilitated second antibody method. Rat GH was measured in aliquots of undiluted or diluted superfusates to determine either basal or stimulated secretion. The antisera (a-hACTH batch No. 2, a-rGH S-4) and the hormones (rGH RP-1 and I-4, hACTH) for both ACTH and GH RIA were provided by NHPP (NIADDK, NIH).

The results from the most active compounds are shown in Table I below.

TABLE 1

In vitro effect of synthetic GH-RH analogs on the GH release used in the superfused pituitary cell system method. Peptides were administered for 3 minutes at $10M^{-9}$ Concentration.

| | Released GH Level | /ng/ml/ Average | Potency % |
|---|---|---|---|
| GH-RH$^{1-29}$ / Standard | 62.50<br>42.50<br>20.50<br>34.50 | 40.00 | 100% |
| Example VII | 89.00<br>122.50 | 105.75 | 264% |
| Example X | 99.00<br>72.50 | 85.75 | 214% |
| Example XII | 60.00<br>58.00 | 59.00 | 148% |
| Example XV | 75.00<br>65.50 | 70.25 | 176% |
| Example XIV | 29.50<br>41.50 | 35.50 | 89% |
| Example XIII/2 | 22.50<br>15.50 | 19.00 | 48% |
| Example XIII/1 | 22.00<br>15.00 | 18.50 | 46% |
| Example IX | 9.00<br>7.50 | 8.25 | 21% |

EXAMPLE XXI

Adult female rats were used and were anesthetized with pentobarbital (6 mg/100 g, b.w.), injected i/p. 20 minutes after the injection of pentobarbital; blood samples were taken from the jugular vein (pretreated level) and immediately thereafter hpGH-RH$^{1-29}$ (as a control) or GH-RH$^{1-29}$ analogs were injected i.v. Blood samples were taken from the jugular vein 5, 15, 60 minutes after the injection. The blood samples were centrifuged, plasma was removed and the GH level was measured by RIA.

The results are tabulated in Table 2 below and are summarized in FIG. 1.

TABLE 2

In vivo Effects of synthetic GHRH analogs on the release of pituitary GH following one single i.v. injection of 1.0 ug/(female) rat.

| | Responses in plasma GH in ng GH/ml | | | |
|---|---|---|---|---|
| time (min.) | −1 | +5 | +15 | +60 |
| hpGHRH (1-29)NH$_2$ (stand.) | 66% | 248% | 137% | 29% |
| Example XV | 36% | 190% | 247% | 33% |
| Example VII | 67% | 670% | 740% | 52% |
| Example XII | 85% | 400% | 290% | 53% |

| Relative Potency (based on the effect of hpGHRH at the actual time) | | | | |
|---|---|---|---|---|
| time (min.) | −1 | +5 | +15 | +60 |
| hpGHRH (1-29)NH$_2$ (stand.) | 100% | 100% | 100% | 100% |
| Example XV | 54% | 76% | 180% | 113% |
| Example VII | 101% | 270% | 540% | 179% |
| Example XII | 128% | 161% | 211% | 182% |

| Absolute Potency (based on the average value of the four samples at −1 min.) average GH level at −1 min. 63.5 ng GH/ml plasma | | | | |
|---|---|---|---|---|
| time (min.) | −1 | +5 | +15 | +60 |
| hpGHRH | 103% | 390% | 215% | 45% |
| Example XV | 56% | 299% | 389% | 52% |
| Example VII | 105% | 1055% | 1165% | 82% |
| Example XII | 134% | 629% | 456% | 83% |

In an experiment on live heifers injected with similar proportions of synthetic peptide and natural GHRH, the synthetic prptide from Example XV was found 3 to 4 times as active as the natural material.

TABLE 3

In vivo effect of synthetic GHRH analogs on the release of GH in male testosterone primed rats. Results were calculated by the 4-point assay method.

Doses injected are in μg/100 g. b.w., i.v.
Tables shows plasma Gh level (ng.ml)

| Standard (GHRH$^{1-29}$) | | Example VII | | Example X | | Example XV | |
|---|---|---|---|---|---|---|---|
| Dose 0.05 | 0.2 | 0.025 | 0.1 | 0.025 | 0.1 | 0.025 | 0.1 |
| 5 minutes after injection | | | | | | | |
| 160 | 370 | 217 | 370 | 216 | 300 | 270 | 900 |
| 540 | 620 | 180 | 870 | 269 | 310 | 180 | 249 |
| 208 | 540 | 210 | 610 | 216 | 440 | 400 | 790 |
| 191 | 610 | 338 | 620 | 250 | 590 | 280 | 160 |
| 450 | 870 | 470 | 410 | 110 | 550 | 160 | 350 |
| 286 | 410 | 320 | 540 | 270 | 430 | 400 | 710 |
| 397 | 560 | 450 | 560 | 86 | 272 | 210 | 377 |

Example VII  sample potency: 196%; potency range: 107–359%
Example X  sample potency: 88%; potency range: 45–174%
Example XV  sample potency: 146%; potency range: 64–331%

15 minutes after injection

| 65 | 112 | 51 | 112 | 100 | 267 | 100 | 200 |
| 241 | 280 | 90 | 510 | 109 | 178 | 70 | 80 |
| 97 | 199 | 52 | 280 | 100 | 238 | 120 | 250 |
| 70 | 261 | 82 | 207 | 75 | 470 | 90 | 70 |
| 161 | 510 | 160 | 161 | 63 | 310 | 70 | 70 |
| 145 | 161 | 108 | 261 | 80 | 200 | 100 | 200 |

TABLE 3-continued

In vivo effect of synthetic GHRH analogs on the release of GH in male testosterone primed rats. Results were calculated by the 4-point assay method.

Doses injected are in μg/100 g. b.w., i.v.
Tables shows plasma Gh level (ng.ml)

| Standard (GHRH$^{1-29}$) | | Example VII | | Example X | | Example XV | |
|---|---|---|---|---|---|---|---|
| Dose 0.05 | 0.2 | 0.025 | 0.1 | 0.025 | 0.1 | 0.025 | 0.1 |
| 149 | 207 | 160 | 199 | 43 | 140 | 80 | 80 |

Example VII  sample potency: 169%; potency range: 77–369%
Example X    sample potency: 165%; potency range: 86–315%
Example XV   sample potency: 53%; potency range: 12–226%

We claim:

1. A polypeptide of the structure $Q^1$-CO-$R_2$-Asp$_3$-Ala$_4$-Ile$_5$-Phe$_6$-Thr$_7$-Asn$_8$-Ser$_9$-Tyr$_{10}$-Arg$_{11}$-Lys$_{12}$-Val$_{13}$-Leu$_{14}$-Gly$_{15}$-Gln$_{16}$-Leu$_{17}$-Ser$_{18}$-Ala$_{19}$-Arg$_{20}$-Lys$_{21}$-Leu$_{22}$-Leu$_{23}$-Gln$_{24}$-Asp$_{25}$-Ile$_{26}$-Nle$_{27}$-Ser$_{28}$-Agm$_{29}$, wherein $Q^1$ is 1-amino-2-(4-hydroxyphenyl)-1-ethyl, 1-amino-2-(imidazol-4-yl)-1-ethyl or 2-(4-hydroxphenyl)-1-ethyl, D-1-amino-2-(4-hydroxyphenyl)-1-ethyl, $R_2$ is D-N-Me-Ala or D-Ala, and the pharmaceutically acceptable addition salts thereof with pharmaceutically acceptable organic or inorganic bases and organic or inorganic acids.

2. A compound of claim 1 wherein $Q^1$ is 2-(4-hydroxyphenyl)-1-ethyl and $R_2$ is D-N-Me-Ala.

3. A compound of claim 1 wherein $Q^1$ is 1-amino-2-(4-hydroxyphenyl)-1-ethyl and $R_2$ is D-Ala.

4. A compound of claim 1 wherein $Q^1$ is D-1-amino-2-(4-hydroxyphenyl)-1-ethyl and $R_2$ is D-N-Me-Ala.

5. A compound of claim 1 wherein $Q^1$ is D-1-amino-2-(4-hydroxyphenyl)-1-ethyl and $R_2$ is D-Ala.

6. A compound of claim 1 wherein $Q^1$ is 1-amino 2-(4-hydroxyphenyl)-1-ethyl and $R_2$ is D-N-Me-Ala.

7. A compound of claim 1 wherein $Q^1$ is 2-(4-hydroxyphenyl)-1-ethyl and $R_2$ is D-Ala.

8. A compound of claim 1 wherein $Q^1$ is 1-amino-2-(imidazol-4-yl)-1-ethyl and $R_2$ is D-Ala.

* * * * *